(12) United States Patent
Emadi et al.

(10) Patent No.: US 7,899,547 B1
(45) Date of Patent: *Mar. 1, 2011

(54) LEVEL-DEPENDENT STIMULATION METHODS AND SYSTEMS

(75) Inventors: Gulam Emadi, Sherman Oaks, CA (US); Leonid M. Litvak, Los Angeles, CA (US)

(73) Assignee: Advanced Bionics, LLC, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/846,641

(22) Filed: Jul. 29, 2010

Related U.S. Application Data

(63) Continuation of application No. 12/022,968, filed on Jan. 30, 2008, now Pat. No. 7,769,467.

(51) Int. Cl.
*A61N 1/00* (2006.01)

(52) U.S. Cl. .......................................................... 607/62

(58) Field of Classification Search .................... 607/62
See application file for complete search history.

(56) References Cited

U.S. PATENT DOCUMENTS

| | | | |
|---|---|---|---|
| 4,532,930 A | 8/1985 | Crosby et al. |
| 4,543,956 A | 10/1985 | Herscovici |
| 4,592,359 A | 6/1986 | Galbraith |
| 4,648,403 A | 3/1987 | Van Compernolle |
| 4,947,844 A | 8/1990 | McDermott |
| 5,193,540 A | 3/1993 | Schulman et al. |
| 5,312,439 A | 5/1994 | Loeb |
| 5,400,590 A | 3/1995 | Wagner et al. |
| 5,824,022 A | 10/1998 | Zilberman et al. |
| 6,016,449 A | 1/2000 | Fischell et al. |
| 6,051,017 A | 4/2000 | Loeb et al. |
| 6,164,284 A | 12/2000 | Schulman et al. |
| 6,185,452 B1 | 2/2001 | Schulman et al. |
| 6,193,539 B1 | 2/2001 | Chang |
| 6,208,894 B1 | 3/2001 | Schulman et al. |
| 6,219,580 B1 | 4/2001 | Faltys et al. |
| 6,272,382 B1 | 8/2001 | Faltys et al. |
| 6,280,873 B1 | 8/2001 | Tsukamoto |
| 6,308,101 B1 | 10/2001 | Faltys et al. |
| 6,381,496 B1 | 4/2002 | Meadows et al. |
| 6,458,171 B1 | 10/2002 | Tsukamoto |

(Continued)

OTHER PUBLICATIONS

Bierer JA and Middlebrooks JC (2002) "Auditory cortical images of cochlear-implant stimuli: dependence on electrode configuration." J Neurophysiol. Jan. 2002; 87(1):478-92.

(Continued)

*Primary Examiner*—Niketa I Patel
*Assistant Examiner*—Shubatra Narayanaswamy
(74) *Attorney, Agent, or Firm*—AdvantEdge Law Group, LLC

(57) ABSTRACT

An exemplary method includes an implantable stimulator simultaneously applying stimulation current to a stimulation site within a patient via at least one stimulating electrode and compensating current via one or more additional electrodes of opposite polarity as the at least one stimulating electrode and dynamically adjusting the simultaneously applied compensating current as a function of a stimulation level of the stimulation current by increasing a stimulation level of the compensating current if the stimulation level of the stimulation current decreases and decreasing the stimulation level of the compensating current if the stimulation level of the stimulation current increases. Corresponding methods and systems are also disclosed.

20 Claims, 12 Drawing Sheets

U.S. PATENT DOCUMENTS

| | | |
|---|---|---|
| 6,487,446 B1 | 11/2002 | Hill et al. |
| 6,501,703 B2 | 12/2002 | Zhou et al. |
| 6,516,227 B1 | 2/2003 | Meadows et al. |
| 6,539,263 B1 | 3/2003 | Schiff et al. |
| 6,553,263 B1 | 4/2003 | Meadows et al. |
| 6,594,525 B1 | 7/2003 | Zierhofer |
| 6,596,439 B1 | 7/2003 | Tsukamoto et al. |
| 6,605,383 B1 | 8/2003 | Wu |
| 6,607,843 B2 | 8/2003 | Ruth, II et al. |
| 6,760,626 B1 | 7/2004 | Boveja |
| 6,938,688 B2 | 9/2005 | Lengauer, Jr. et al. |
| 6,980,864 B2 | 12/2005 | Faltys et al. |
| 7,082,332 B2 | 7/2006 | Blamey et al. |
| 7,340,308 B1 | 3/2008 | Clopton et al. |
| 2005/0101878 A1* | 5/2005 | Daly et al. .................. 600/559 |

OTHER PUBLICATIONS

Kral A et al. (1998) "Spatial resolution of cochlear implants: the electrical field and excitation of auditory afferents." Hear Res. Jul. 1998; 121(1-2):11-28.

Mens LH, Berenstein CK. (2005). "Speech perception with mono- and quadrupolar electrode configurations: a crossover study." Otol Neurotol. Sep. 2005; 26(5):957-64.

Miller CA et al.(2003). "Electrode configuration influences action potential initiation site and ensemble stochastic response properties." Hear Res. Jan. 2003; 175(1-2):200-14.

Miyoshi S et al.(1996). "Proposal of a new auditory nerve stimulation method for cochlear prosthesis." Artif Organs. Aug. 1996; 20(8):941-6.

Morris DJ and Pfingst BE (2000). "Effects of electrode configuration and stimulus level on rate and level discrimination with cochlear implants." J Assoc Res otolaryngol. Nov. 2000;1(3):211-23.

Non-Final Office Action received in U.S. Appl. No. 12/022,968, Oct. 5, 2009.

* cited by examiner

LEVEL-DEPENDENT STIMULATION METHODS AND SYSTEMS

The present application is a continuation application of U.S. patent application Ser. No. 12/022,968 by Gulam Emadi et al., filed on Jan. 30, 2008, and entitled "Level-Dependent Stimulation Methods and Systems," which application is now U.S. Pat. No. 7,769,467, issued Aug. 3, 2010, and is incorporated herein by reference in its entirety.

BACKGROUND INFORMATION

A wide variety of medical conditions and disorders have been successfully treated using implantable stimulators. Such implantable stimulators include, but are not limited to, implantable cochlear stimulators, spinal cord stimulators, deep brain stimulators, and microstimulators.

To illustrate, the sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that acoustic signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce acoustic signals into auditory nerve impulses. Thus, people who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems seek to bypass the hair cells in the cochlea by presenting electrical stimulation directly to the auditory nerve fibers. Direct stimulation of the auditory nerve fibers leads to the perception of sound in the brain and at least partial restoration of hearing function. To facilitate direct stimulation of the auditory nerve fibers, an array of electrodes may be implanted in the cochlea. A sound processor processes and translates an incoming sound into electrical stimulation pulses applied by these electrodes which directly stimulate the auditory nerve.

Electrical stimulation generated and applied via an implantable stimulator is often implemented in a "monopolar" configuration, in which a relatively remote ground electrode provides the return path for the current delivered by an active stimulating electrode. However, monopolar stimulation produces relatively broad spatial regions of excitation. Depending on the overall stimulation level, such broad excitation patterns can lead to a deterioration in stimulator performance.

Hence, some implantable stimulators are configured to focus or narrow the excitation fields resulting from electrical stimulation by applying compensating current via additional electrodes. Additionally or alternatively, the excitation fields may be narrowed by moving the location of the ground electrode closer to the stimulating electrode. However, these approaches used a "fixed" amount of excitation narrowing across all stimulation levels, and therefore do not provide the optimum solution in terms of stimulator performance.

SUMMARY

Methods of applying stimulation to a stimulation site within a patient include applying stimulation current to the stimulation site via at least one stimulating electrode, applying compensating current configured to affect at least one excitation field caused by the stimulation current via one or more additional electrodes, and dynamically adjusting the compensating current as a function of an amplitude of the stimulation current.

Systems for applying stimulation to a stimulation site within a patient include an implantable stimulator, at least one stimulating electrode electrically coupled to the implantable stimulator, and one or more additional electrodes electrically coupled to the implantable stimulator. The stimulator is configured to apply stimulation current to the stimulation site via the at least one stimulating electrode, apply compensating current configured to affect at least one excitation field caused by the stimulation current via the one or more additional electrodes, and dynamically adjust the compensating current as a function of an amplitude of the stimulation current.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

DETAILED DESCRIPTION

Methods and systems for applying stimulation current to a stimulation site within a patient are described herein. In some examples, an implantable stimulator is coupled to at least one stimulating electrode and to one or more additional electrodes configured to act as compensating electrodes. The stimulator is configured to apply stimulation current to the stimulation site via the at least one stimulating electrode and to apply compensating current configured to affect at least one excitation field caused by the stimulation current via the compensating electrodes. The stimulator may be further configured to dynamically adjust the compensating current as a function of an amplitude of the stimulation current. In this manner, the excitation fields caused by the stimulation current may be narrowed or focused at relatively low stimulation levels in order to improve stimulator performance and broadened at relatively high stimulation levels to minimize the effects of side lobes within the spatial pattern of the excitation fields. For example, in the case of implantable cochlear stimulators, selective narrowing of the excitation fields at relatively low stimulation levels is desirable because this behavior is akin to the functioning of the normal auditory system, where the excitation pattern of the basilar membrane is narrowed selectively for low acoustic excitations of the outer hair cells.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
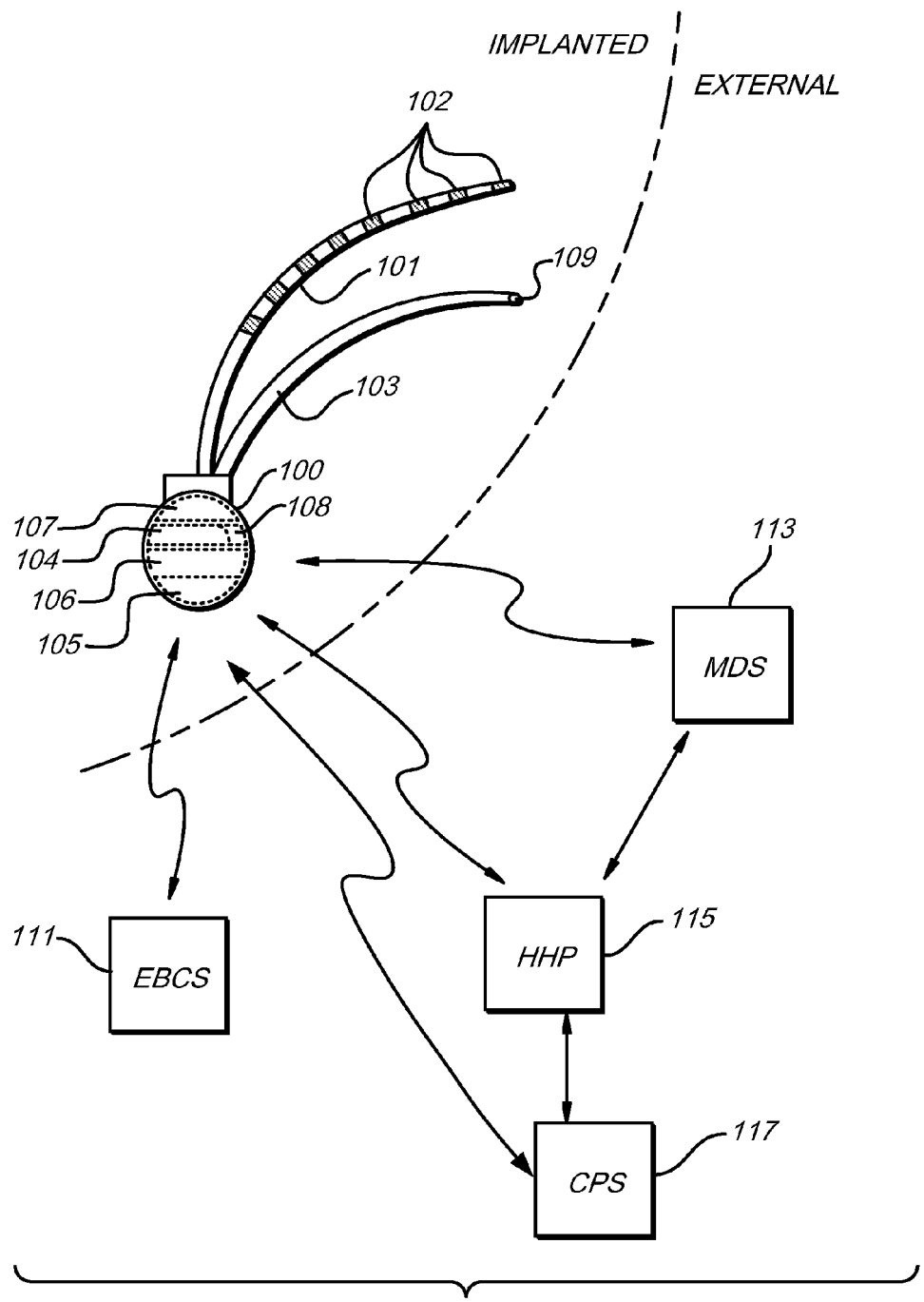
FIG. 1 illustrates an exemplary stimulator that may be used to apply a stimulus to a stimulation site within a patient according to principles described herein.

To facilitate an understanding of the methods and systems described herein, an exemplary implantable stimulator will now be described in connection with FIG. 1. FIG. 1 illustrates an exemplary stimulator 100 that may be used to apply a stimulus to a stimulation site within a patient, e.g., an electrical stimulation of the stimulation site, an infusion of one or more drugs at the stimulation site, or both. The electrical stimulation function of the stimulator 100 will be described first, followed by an explanation of the possible drug delivery function of the stimulator 100. It will be understood, however, that the stimulator 100 may be configured to provide only electrical stimulation, only drug stimulation, both types of stimulation, or any other type of stimulation as best suits a particular patient.

The exemplary stimulator 100 shown in FIG. 1 is configured to provide electrical stimulation to one or more stimulation sites within a patient and may include a lead 101 coupled thereto. In some examples, the lead 101 includes a number of electrodes or electrode contacts 102 disposed thereon through which electrical stimulation current may be applied to a stimulation site. It will be recognized that the lead 101 may include any number of electrodes 102 arranged in any configuration as may serve a particular application. Moreover, it will be recognized that the electrodes 102 described herein may perform any function as best serves a particular application such as, but not limited to, stimulating and/or sensing.

In some examples, as shown in FIG. 1, the lead 101 is coupled directly to the stimulator 100. Alternatively, the lead 101 and/or the stimulator 100 may include one or more connector assemblies and/or lead extension assemblies configured to facilitate coupling of the lead 101 to the stimulator.

As illustrated in FIG. 1, the stimulator 100 includes a number of components. It will be recognized that the stimulator 100 may include additional and/or alternative components as best serves a particular application. A power source 105 is configured to output voltage used to supply the various components within the stimulator 100 with power and/or to generate the power used for electrical stimulation. The power source 105 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like.

In some examples, the power source 105 may be recharged using an external charging system. One type of rechargeable power supply that may be used is described in U.S. Pat. No. 6,596,439, which is incorporated herein by reference in its entirety. Other battery construction techniques that may be used to make the power source 105 include those shown, e.g., in U.S. Pat. Nos. 6,280,873; 6,458,171; 6,605,383; and 6,607,843, all of which are incorporated herein by reference in their respective entireties.

The stimulator 100 may also include a coil 108 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 105.

For example, an external battery charging system (EBCS) 111 may be provided to generate power that is used to recharge the power source 105 via any suitable communication link. Additional external devices including, but not limited to, a hand held programmer (HHP) 115, a clinician programming system (CPS) 117, and/or a manufacturing and diagnostic system (MDS) 113 may also be provided and configured to activate, deactivate, program, and/or test the stimulator 100 via one or more communication links. It will be recognized that the communication links shown in FIG. 1 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 100. It will be recognized that any suitable communication link may be used among the various devices illustrated.

The external devices shown in FIG. 1 are merely illustrative of the many different external devices that may be used in connection with the stimulator 100. Furthermore, it will be recognized that the functions performed by any two or more of the external devices shown in FIG. 1 may be performed by a single external device.

The stimulator 100 may also include electrical circuitry 104 configured to generate the electrical stimulation current that is delivered to a stimulation site via one or more of the electrodes 102. For example, the electrical circuitry 104 may include one or more processors, capacitors, integrated circuits, resistors, coils, and/or any other component configured to generate electrical stimulation current.

Additionally, the exemplary stimulator 100 shown in FIG. 1 may be configured to provide drug stimulation to a patient by applying one or more drugs at a stimulation site within the patient. To this end, a pump 107 may also be included within the stimulator 100. The pump 107 is configured to store and dispense one or more drugs, for example, through a catheter 103. The catheter 103 is coupled at a proximal end to the stimulator 100 and may have an infusion outlet 109 for infusing dosages of the one or more drugs at the stimulation site. In some embodiments, the stimulator 100 may include multiple catheters 103 and/or pumps 107 for storing and infusing dosages of the one or more drugs at the stimulation site.

The stimulator 100 may also include a programmable memory unit 106 configured to store one or more stimulation parameters. The stimulation parameters may include, but are not limited to, electrical stimulation parameters, drug stimulation parameters, and other types of stimulation parameters. The programmable memory unit 106 allows a patient, clinician, or other user of the stimulator 100 to adjust the stimulation parameters such that the stimulation applied by the stimulator 100 is safe and efficacious for treatment of a particular patient. The programmable memory unit 106 may include any type of memory unit such as, but not limited to, random access memory (RAM), static RAM (SRAM), a hard drive, or the like.

The electrical stimulation parameters may control various parameters of the stimulation current applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

The stimulator 100 of FIG. 1 is illustrative of many types of stimulators that may be used to apply a stimulus to a stimulation site. For example, the stimulator 100 may include an implantable cochlear stimulator. An exemplary cochlear implant system 120 will be described in connection with FIG. 2. Exemplary cochlear implant systems suitable for use as described herein include, but are not limited to, those disclosed in U.S. Pat. Nos. 5,400,590; 4,532,930; 4,592,359; 4,947,844; and 5,824,022; 6,219,580; 6,272,382; and 6,308,101. All of these listed patents are incorporated herein by reference in their respective entireties.

Figure 2:
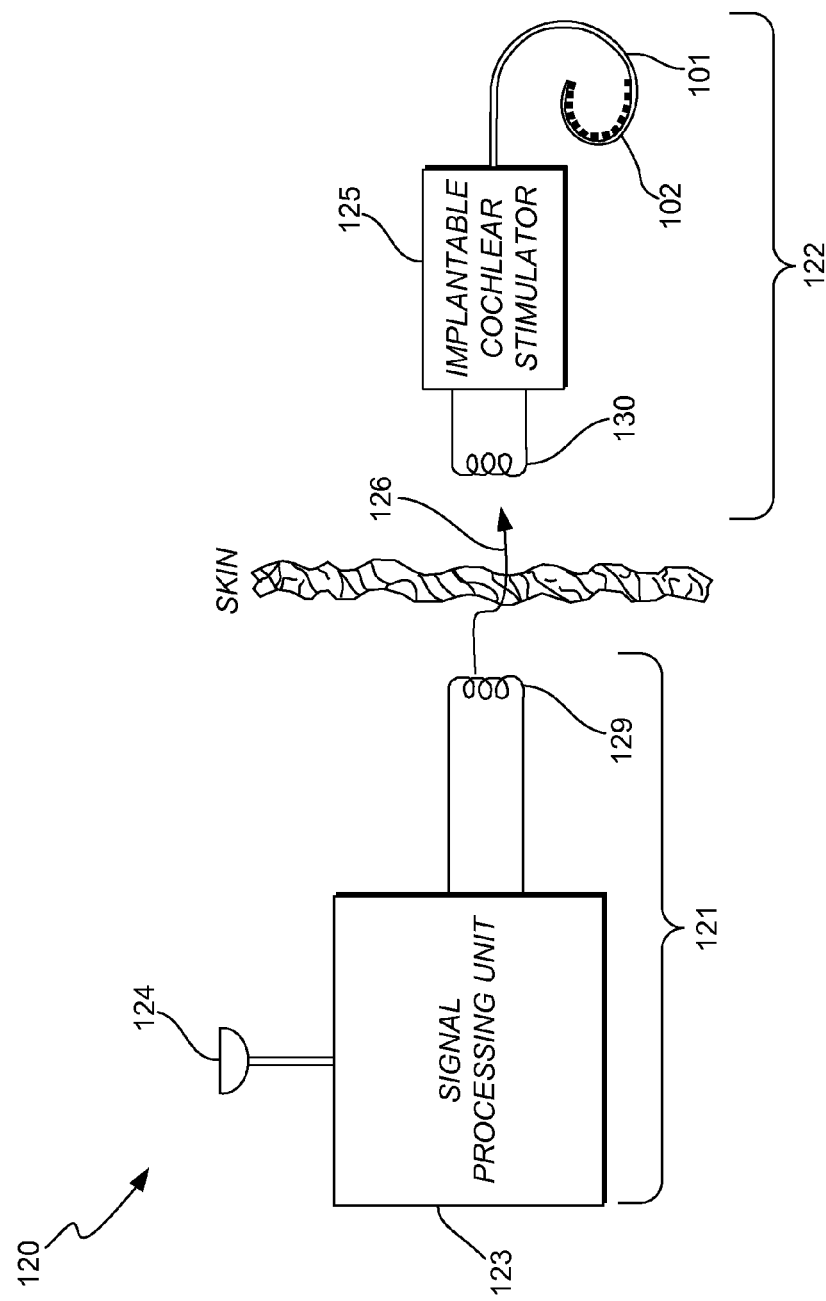
FIG. 2 illustrates an exemplary cochlear implant system according to principles described herein.

As shown in FIG. 2, the cochlear implant system 120 includes an external signal processor portion 121 and an implanted cochlear stimulation portion 122. The signal processor portion 121 may include a signal processing unit 123, a microphone 124, and/or additional circuitry as best serves a particular application. The cochlear stimulation portion 122 may include an implantable cochlear stimulator (ICS) 125, a number of electrodes 102 disposed on a lead 101, and/or additional circuitry as best serves a particular application. It will be recognized that the signal processor portion 121 may alternatively be located internal to the patient.

The microphone 124 of FIG. 2 is configured to sense acoustic signals and convert the sensed signals to corresponding electrical signals. The electrical signals are sent to the signal processing unit 123 over an electrical or other suitable link. Alternatively, the microphone 124 may be connected directly to, or integrated with, the signal processing unit 123.

The signal processing unit 123 may include any combination of hardware, software, and/or firmware as best serves a particular application. For example, the signal processing unit 123 may include one or more processors, digital signal processors (DSPs), filters, memory units, etc.

In some examples, the signal processing unit 123 may be configured to process the converted acoustic signals in accordance with a selected speech processing strategy to generate appropriate control signals or stimulation parameters for controlling the ICS 125. It will be recognized that the signal processing unit 123 shown in FIG. 2 is merely illustrative of the many different signal processing units that may be used in connection with the present systems and methods. For example, the signal processing unit 123 may include a behind-the-ear (BTE) unit configured to be positioned behind the ear. Alternatively, the signal processing unit 123 may include a portable speech processor (PSP) device, a conventional hearing aid, or any other type of signal processing unit.

The lead 101 of FIG. 2 is adapted to be inserted within a duct of a patient's cochlea. As shown in FIG. 2, the lead 101 includes a plurality of electrodes 102 disposed along its length. It will be recognized that any number of electrodes 102 may be disposed along the lead 101 as may serve a particular application.

Each of the electrodes 102 is electrically coupled to the ICS 125. Electronic circuitry within the ICS 125 may therefore be configured to apply stimulation current to selected pairs or groups of electrodes 102 in accordance with a specified stimulation pattern controlled by the signal processing unit 123.

As mentioned, the ICS 125 and lead 101 may be implanted within the patient while the signal processing unit 123 and the microphone 124 are configured to be located outside the patient, e.g., behind the ear. Hence, the ICS 125 and the signal processing unit 123 may be transcutaneously coupled via a suitable data or communications link 126. The communications link 126 allows power and control signals to be sent from the signal processing unit 123 to the ICS 125. In some embodiments, data and status signals may also be sent from the ICS 125 to the signal processing unit 123.

The external and implantable portions of the cochlear implant system 120 may each include one or more coils configured to transmit and receive power and/or control signals via the data link 126. For example, the external portion 121 of the cochlear implant system 120 may include an external coil 129 and the implantable portion of the cochlear implant system 122 may include an implantable coil 130. The external coil 129 and the implantable coil 130 may be inductively coupled to each other, thereby allowing data and power signals to be wirelessly transmitted between the external portion and the implantable portion of the cochlear implant system 120.

Additional or alternative devices that may be used as the implantable stimulator 100 include, but are not limited to, implantable pulse generators (IPGs), spinal cord stimulators, deep brain stimulators, microstimulators, and/or any other type of implantable stimulator configured to deliver a stimulus at a stimulation site within a patient. Exemplary IPGs suitable for use as described herein include, but are not limited to, those disclosed in U.S. Pat. Nos. 6,381,496, 6,553, 263; and 6,760,626. Exemplary spinal cord stimulators suitable for use as described herein include, but are not limited to, those disclosed in U.S. Pat. Nos. 6,501,703; 6,487,446; and 6,516,227. Exemplary deep brain stimulators suitable for use as described herein include, but are not limited to, those disclosed in U.S. Pat. Nos. 6,938,688; 6,016,449; and 6,539, 263. Exemplary microstimulators suitable for use as described herein include, but are not limited to, those disclosed in U.S. Pat. Nos. 6,193,539; 5,193,540; 5,312,439; 6,185,452; 6,164,284; 6,208,894; and 6,051,017.

As mentioned, typical implantable stimulators 100 generate and apply monopolar stimulation wherein a relatively remote or distant ground electrode provides the return path for current delivered by one or more stimulating electrodes to a stimulation site. The resultant spatial excitation field of the stimulation site is relatively broad. Depending on the overall stimulation level, such broad excitation patterns can lead to a deterioration in stimulator performance. For example, even at relatively low stimulation levels, monopolar stimulation may result in undesirable channel interaction and inadequate spectral resolution. In the case of implantable cochlear stimulators, monopolar stimulation may result in sub-optimal speech recognition.

Figure 3:
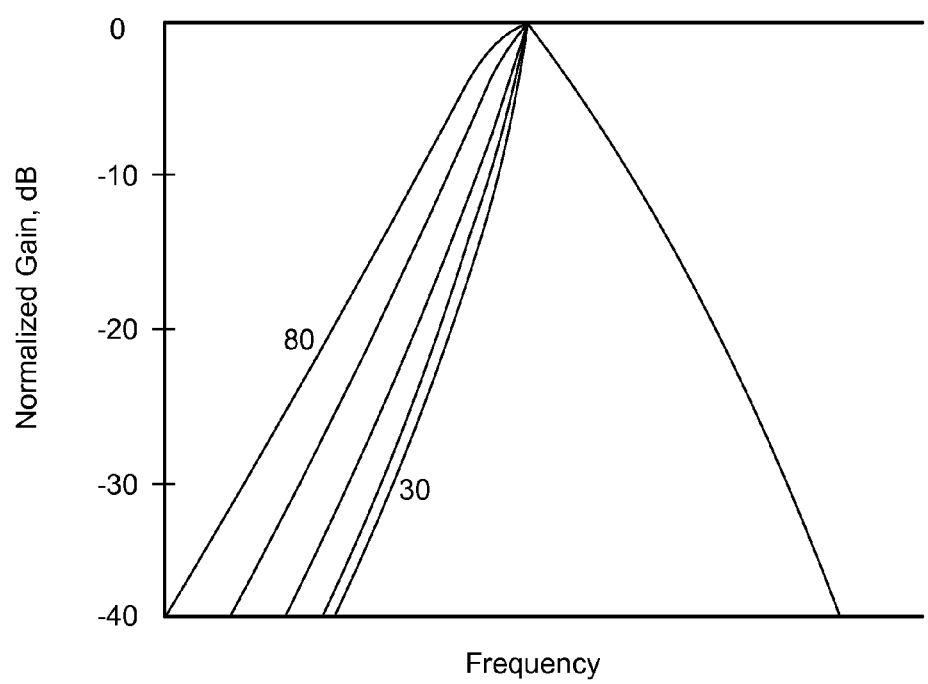
FIG. 3 is a graph of a stimulation level-dependent spread of excitation fields in a normal cochlea according to principles described herein.

Hence, it is believed that a focusing or narrowing of the excitation fields generated by an implantable stimulator 100 at relatively low stimulation levels may be useful in improving stimulator performance. A biological basis for this type of strategy is rooted in the spatial sharpening of activity generated by the outer hair cells in the cochlea at relatively low levels of acoustic stimulation. For example, FIG. 3 is a graph of a stimulation level-dependent spread of excitation fields in a normal cochlea. Sinusoidal inputs ranging from 30 to 80 dB were presented to the subject cochlea of FIG. 3 and the resultant excitation fields were measured and normalized. As shown in FIG. 3, the highest input level (80 dB) resulted in the broadest excitation field and the lowest input level (30 dB) resulted in the most narrow excitation field. Hence, FIG. 3 illustrates that excitation fields in a normal cochlea are more narrow (i.e., have a higher "Q" factor) for lower levels of stimulation.

In some examples, the excitation field generated by a particular electrode that is coupled to a stimulator 100 may be narrowed by using a "multipolar" electrode configuration. In a multipolar electrode configuration, one or more additional electrodes are provided through which compensating current is delivered. These additional electrodes will be referred to herein as "compensating electrodes."

Figure 4:
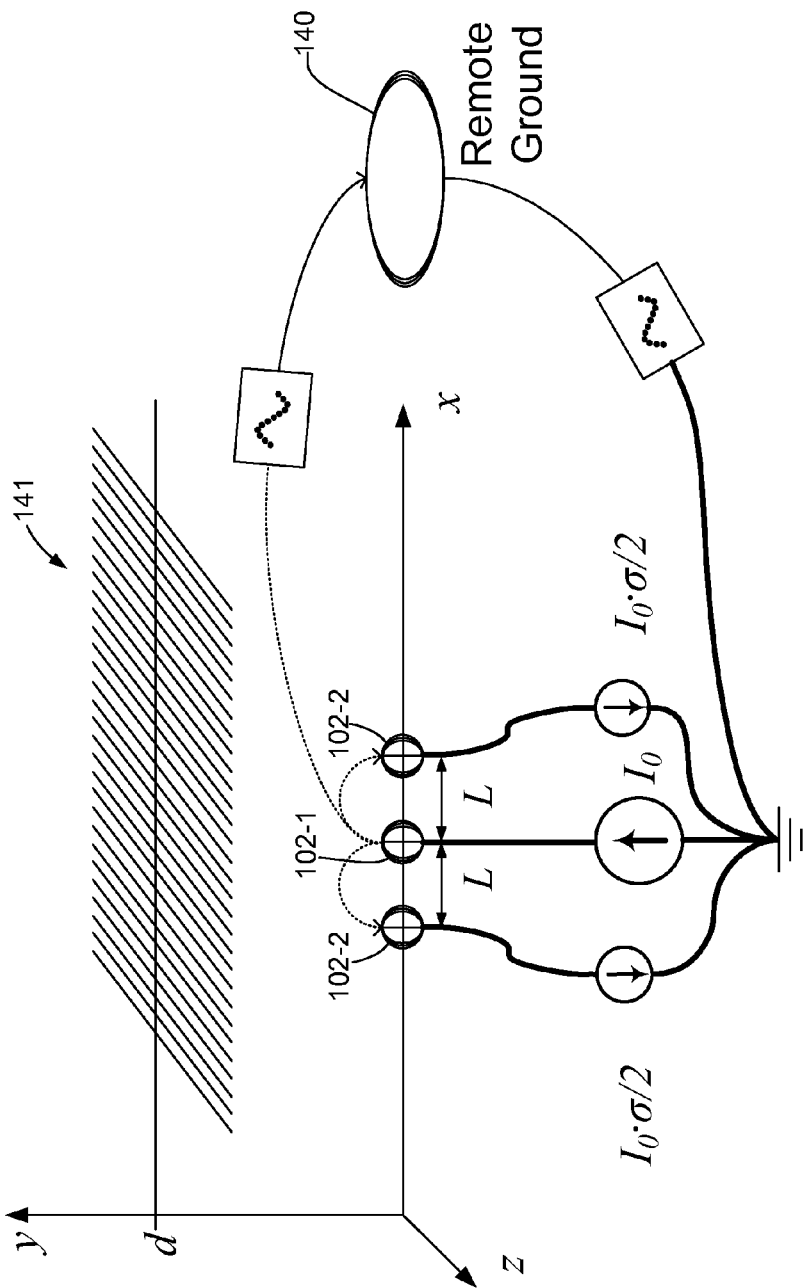
FIG. 4 illustrates an exemplary multipolar electrode configuration according to principles described herein.

FIG. 4 illustrates an exemplary multipolar electrode configuration that may be used in connection with the systems and methods described herein. As shown in FIG. 4, the multipolar electrode configuration includes a number of active stimulating electrodes 102 and a remote ground electrode 140 configured to provide a return path for the current delivered by the stimulating electrodes 102.

The particular multipolar configuration shown in FIG. 4 is also referred to as "tripolar" or as "quadripolar" because, for a given stimulation site, three electrodes are engaged simultaneously, in addition the remote ground. The polarity of electrode 102-1 may be configured as anodic (+) and the polarity of electrodes 102-2 may be configured as cathodic (−), or vice versa. It will be understood that the number of stimulating electrodes 102 within the multipolar configuration may vary as may serve a particular application. Alternative multipolar configurations will be described in more detail below. However, for illustrative purposes only, it will be assumed in many of the examples given herein that the multipolar configuration is tripolar.

In some examples, the electrodes 102 are collinearly positioned a certain distance d away from a stimulation site 141 (e.g., a body of neurons). For example, the electrodes 102 shown in FIG. 4 are collinearly located along a particular axis (e.g., the x-axis). Moreover, as shown in FIG. 4, the electrodes 102 may be separated one from another by a separation distance L. The separation distance L and the distance d may vary as may serve a particular application. It will also be recognized that the electrodes 102 may be positioned in any alternative arrangement as may serve a particular application. For example, the electrodes 102 may be located within different planes.

As shown in FIG. 4, a stimulation current $I_0$ may be applied to the stimulation site 141 via the center electrode 102-1. The stimulation current $I_0$ may be generated by the stimulator 100 and may be in accordance with one or more stimulation parameters as may serve a particular application.

As shown in FIG. 4, current may also be applied via the compensating electrodes 102-2 in order to narrow the excitation field caused by the center electrode 102-1. The compensating current is opposite in phase as the stimulation current $I_0$ and may be represented by $I_0*\sigma/2$, wherein $\sigma$ represents a programmable multiplication factor ranging from 0 to 1. Hence, the total compensating current applied via electrodes 102-2 may be varied from 0 to $I_0$. The programmable multiplication factor $\sigma$ will be referred to herein as a "focusing factor."

For example, the focusing factor $\sigma$ may be set to 0 in order to prevent current from being applied via the compensating electrodes 102-2. In this manner, the center electrode 102-1 may be configured to apply current in a fully monopolar configuration. The focusing factor $\sigma$ may be programmed to be equal to 1 in order to apply an equal amount of current via the compensating electrodes 102-2 as is applied via the center electrode 102-1. In this manner, the electrodes 102 may be configured to operate in a fully multipolar configuration.

In some examples, the electrodes 102 may be programmed to operate in a "partially multipolar" configuration wherein the total amount of current applied by the compensating electrodes 102-2 is greater than 0 and less than $I_0$. Exemplary partially multipolar configurations will be described in more detail below. The term "multipolar" will be used herein to generally refer to fully multipolar and partially multipolar configurations, unless otherwise specified. However, for illustrative purposes only, many of the examples given herein will be described in terms of fully tripolar and partially tripolar configurations.

The compensating electrodes 102-2 shown in FIG. 4 are both configured to apply an equal amount of compensating current (i.e., $I*\sigma/2$) for illustrative purposes only. It will be recognized that the compensating electrodes 102-2 may alternatively be configured to apply different amounts of compensating current as may serve a particular application.

Figure 5:
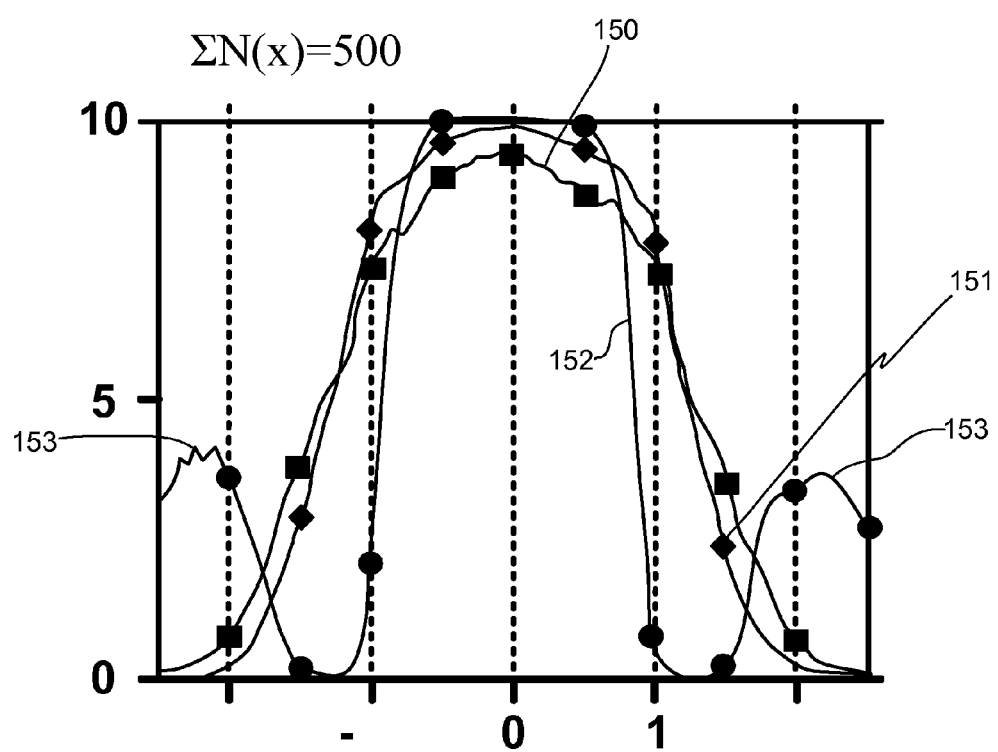
FIG. 5 is a graph illustrating the effect of varying the focusing factor σ on the neuronal response fields elicited by the excitation fields that are caused by stimulation current applied via electrodes according to principles described herein.

FIG. 5 is a graph illustrating the effect of varying the focusing factor σ on the neuronal response fields elicited by the excitation fields that are caused by stimulation current applied via electrodes 102. The curve labeled 150 represents the excitation field corresponding to a monopolar configuration (i.e., a σ=0). As shown in FIG. 5, the monopolar curve 150 is relatively broad. Curve 151 represents the excitation field corresponding to a partially tripolar configuration (i.e., 0<σ<1). As shown in FIG. 5, the partially tripolar curve 151 is more narrow than the monopolar curve 150. Curve 152 represents the excitation field corresponding to a fully tripolar configuration (i.e., σ=0). As shown in FIG. 5, the fully tripolar configuration curve 152 is the most narrow of the three curves.

However, at relatively higher overall levels of stimulation, side lobes may appear in the spatial pattern of an excitation field as the value of the focusing factor σ is increased. For example, the fully tripolar configuration curve 152 in FIG. 5 includes two side lobes 153. These side lobes are often undesirable and may result in signal distortion and frequency artifacts.

Hence, the systems and methods described herein provide for level-dependent calibration of the focusing factor σ so as to obtain optimal excitation fields across a range of stimulation levels. As will be described in more detail below, σ may be dynamically increased for relatively lower levels of electrical stimulation and dynamically decreased for relatively higher levels of stimulation. In this manner, the excitation fields produced by the electrical stimulation may be relatively more focused at lower stimulation levels in order to improve the effectiveness of the stimulation and relatively more broad at higher stimulation levels in order to minimize the formation of side lobes.

To illustrate the systems and methods herein, a number of examples will be given in connection with cochlear implant systems. However, it will be recognized that these examples are merely illustrative and that the systems and methods described herein may be used in connection with any type of implantable stimulator.

Figure 6:
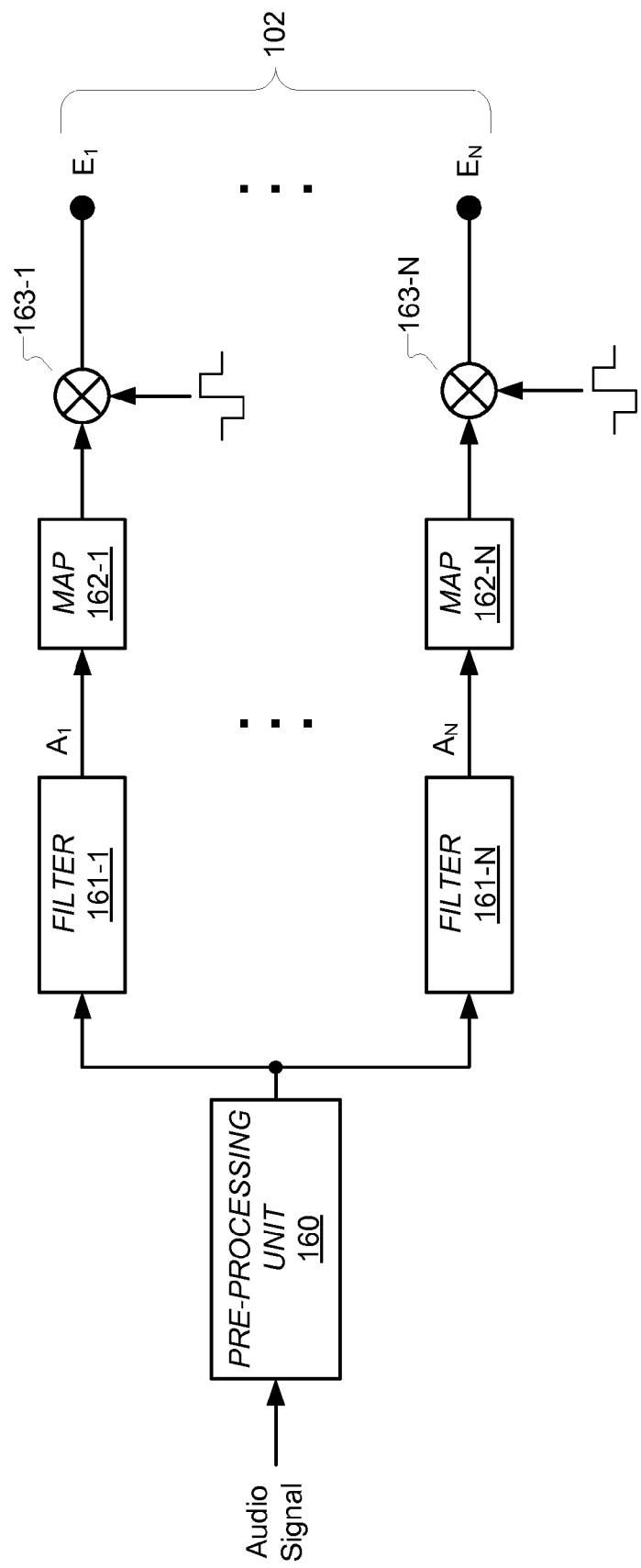
FIG. 6 is a functional block diagram of an exemplary cochlear implant processing strategy wherein electrical stimulation is applied via a monopolar electrode configuration according to principles described herein.

FIG. 6 is a functional block diagram of an exemplary cochlear implant processing strategy wherein electrical stimulation is applied via a monopolar electrode configuration. It will be recognized that the functions shown in FIG. 6 are merely illustrative and that additional or alternative functions may be performed within the processing strategy. The functions may be performed by one or more components within the signal processing unit 123, for example.

As shown in FIG. 6, an audio signal may be first input into a pre-processing unit 160. The pre-processing unit 160 may include one or more components configured to amplify the audio signal, convert the signal to a digital signal, filter the digital signal with a pre-emphasis filter, and subject the digital signal to automatic gain control.

The digital signal is then input into N band-pass filters (e.g., 161-1 through 161-N, collectively referred to herein as 161) such that the digital signal is divided into N frequency channels or bands. Each filter 161 outputs an envelope signal having an amplitude $A_1$ through $A_N$.

The signal within each frequency channel is then input into a mapping stage (e.g., 162-1 through 162-N, collectively referred to herein as 162). The mapping stages 162 are configured to map the amplitude of the signals within each channel to corresponding current levels in accordance with a mapping function that may be set by a clinician or other user of the cochlear implant system. The current levels are then used by multiplication blocks (e.g., 163-1 through 163-N, collectively referred to herein as 163) to construct stimulation pulse trains that are delivered to corresponding electrodes 102 (e.g., $E_1$ through $E_N$) in a monopolar configuration.

Figure 7:
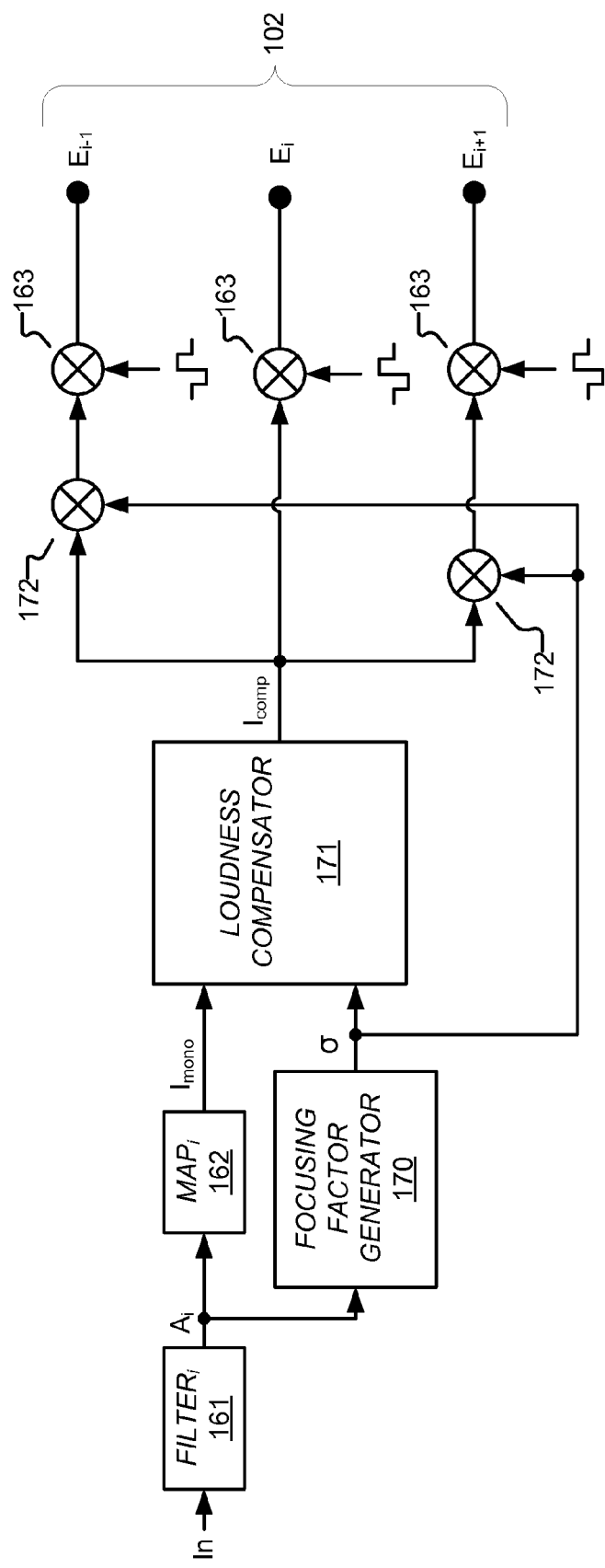
FIG. 7 illustrates an exemplary system configured to dynamically focus one or more excitation fields according to principles described herein.

As described hereinabove, the excitation field produced by the electrical stimulation that is applied via a particular electrode 102 shown in FIG. 6 may be narrowed or focused by also applying compensating current via one or more additional electrodes 102. FIG. 7 illustrates an exemplary system configured to dynamically focus one or more excitation fields. As will be described in more detail below, the system of FIG. 7 is configured to narrow stimulation current applied via a center electrode $E_i$ by applying compensating current via one or more additional electrodes (e.g., $E_{i-1}$ and $E_{i+1}$).

A single frequency channel of a cochlear implant system is shown in FIG. 7 for illustrative purposes. However, it will be recognized that the system may include any number of frequency channels and may be incorporated into any type of implantable stimulator as may serve a particular application.

As shown in FIG. 7, a focusing factor generator 170 may be configured to analyze the amplitude of the envelope signal output by the filter 161 and generate the aforementioned focusing factor σ as a function of the amplitude of the envelope signal. Hence, as will be described in more detail below, the focusing factor σ is also a function of the amplitude of the current output via the center electrode $E_i$. The focusing factor generator 170 may include any suitable combination of hardware, software, and/or firmware configured to process a digital and/or analog signal. For example, the focusing factor generator 170 may include a processor.

Figure 8:
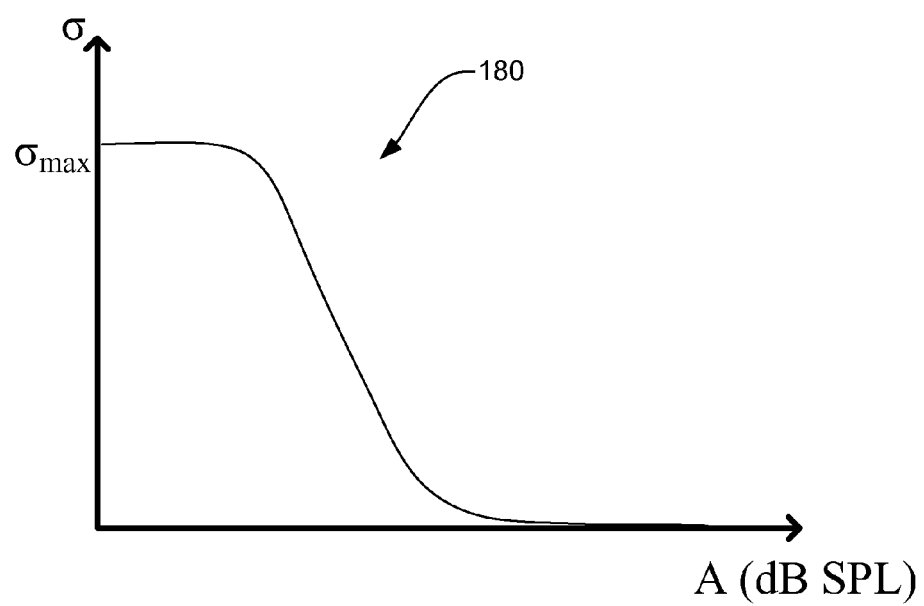
FIG. 8 illustrates an exemplary focusing function that may be used by the focusing factor generator to generate the focusing factor σ according to principles described herein.

In some examples, the focusing factor σ is computed according to a pre-determined focusing function. FIG. 8 illustrates an exemplary focusing function 180 that may be used by the focusing factor generator 170 to generate the focusing factor σ. Focusing function 180 shows an exemplary relationship between amplitude in a given frequency channel and the focusing factor σ. As shown in FIG. 8, the value of the focusing factor σ decreases as the amplitude within the channel increases. It will be recognized that the focusing function 180 shown in FIG. 8 is merely illustrative and that the exact function may be adjusted as desired to achieve maximum benefit to a particular patient.

Returning to FIG. 7, the amplitude of the envelope signal output by the filter 161 is also used by the mapping function 162 to determine and output a current in a similar manner as that described in connection with FIG. 6. In the absence of compensating current, the current output by the mapping function 162 is equal to that output by the monopolar configuration of FIG. 6. Hence, the current output by the mapping function 162 will be referred to as "monopolar current $I_{mono}$."

The output of the mapping function 162 and the focusing factor σ are then input into a loudness compensator 171, which is configured to output a compensated current $I_{comp}$. The loudness compensator 171 may include any suitable combination of hardware, software, and/or firmware as may serve a particular application.

Depending on the amount of focusing, the overall current level may need to be adjusted to maintain equivalent loudness as perceived by the patient. Hence, as the focusing factor σ is increased, the loudness compensator 171 may be configured to increase the current that is output to the center electrode $E_i$ and the compensating electrodes $E_{i-1}$ and $E_{i+1}$. In other types of stimulators, any suitable response compensator may be used in place of the loudness compensator 171.

Figure 9:
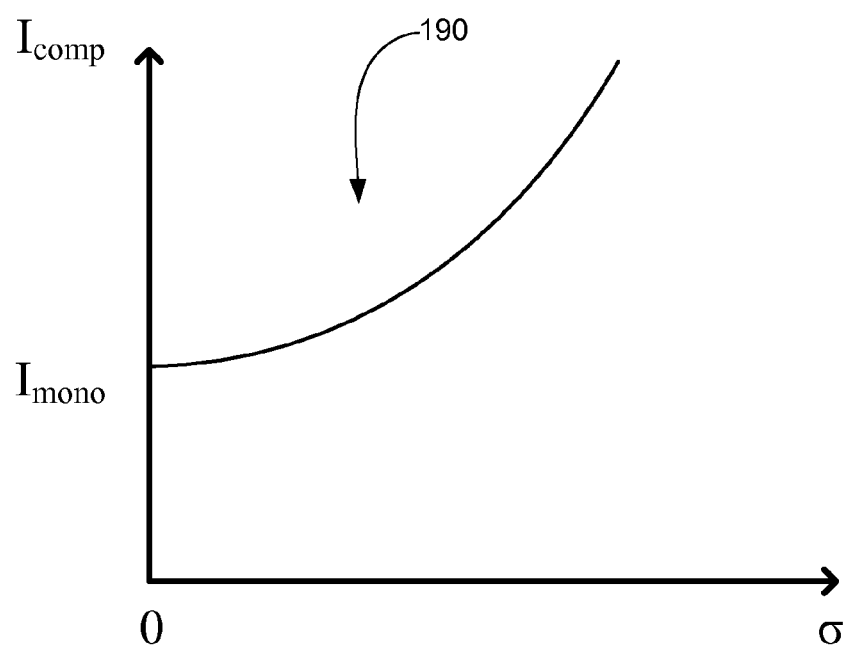
FIG. 9 illustrates an exemplary loudness compensation function that may be used by a loudness compensator according to principles described herein.

In some examples, the loudness compensator 171 may be configured to adjust the monopolar current $I_{mono}$ in accordance with a loudness compensation function. FIG. 9 illustrates an exemplary loudness compensation function 190 that may be used by the loudness compensator 171. As shown in FIG. 9, if the focusing factor σ is 0, $I_{comp}$ is equal to $I_{mono}$. As the focusing factor σ is increased, the current output by the loudness compensator 171 is increased according to the equation $$I_{comp} = \frac{I_{mono}}{1 - k\sigma},$$

where k is an adjustable interaction coefficient. It will be recognized that the loudness compensation function may be adjusted as may serve a particular application or patient.

Returning to FIG. 7, the full current $I_{comp}$ output by the loudness compensator 171 is then delivered to the center electrode $E_i$. Current equal to the full current $I_{comp}$ scaled down by the focusing factor σ is also applied in a simultaneous or time-interleaved manner by the compensating electrodes $E_{i-1}$ and $E_{i+1}$. To this end, a multiplication block 172 corresponding to each compensating electrode $E_{i-1}$ and $E_{i+1}$ may be provided. Each multiplication block 172 is configured to scale the current $I_{comp}$ by the focusing factor σ in a manner similar to that described hereinabove.

Hence, if the amplitude of an input signal increases, the system of FIG. 7 is configured to decrease the focusing factor σ in order to prevent the formation of side lobes in the resultant excitation field. Likewise, if the amplitude of an input signal decreases, the system of FIG. 7 is configured to increase the focusing factor σ in order to narrow the resultant activation field.

Figure 10:
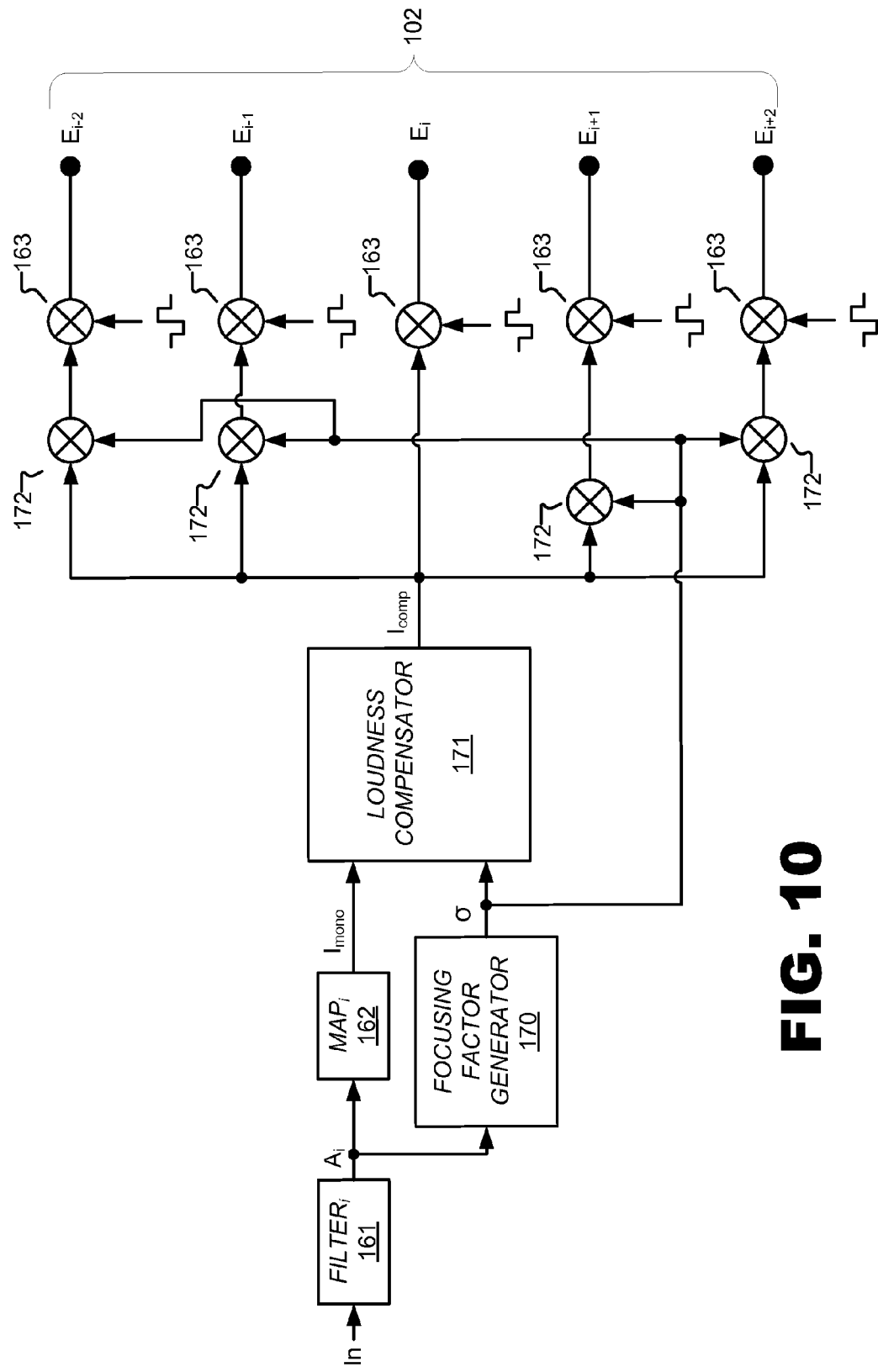
FIG. 10 illustrates an alternative excitation field narrowing configuration according to principles described herein.

It will be recognized that compensating current may be applied via any number of compensating electrodes 102. For example, FIG. 10 illustrates an alternative configuration wherein compensating current is delivered via four electrodes ($E_{i-2}$, $E_{i-1}$, $E_{i+1}$, and $E_{i+2}$). It will be recognized also that the compensating electrodes need not be immediately adjacent to the center electrode. For example, compensation current may be applied via electrodes $E_{i-3}$ and $E_{i+3}$, etc. Hence, in this example, $I_{comp}$ is fully delivered via the center electrode $E_i$ while compensating current equal to the full current $I_{comp}$ scaled down by the focusing factor σ may be applied by the compensating electrodes $E_{i-2}$, $E_{i-1}$, $E_{i+1}$, and $E_{i+2}$.

In some examples, the compensating current delivered via the compensating electrodes $E_{i-2}$, $E_{i-1}$, $E_{i+1}$, and $E_{i+2}$ may be further scaled as a function of distance from the center electrode $E_i$. For example, if $E_i$ receives current $I_{comp}$, then $E_{i+1}$ and $E_{i-1}$ might each receive $0.4*\sigma*I_{comp}$, and $E_{i+2}$ and $E_{i-2}$ might each receive $0.1*\sigma*I_{comp}$, etc.

In some examples, the systems and methods described herein may be used in connection with a current-steering stimulation strategy. Current-steering may be used in configurations wherein a desired stimulation site is located spatially in between two electrodes. To effectively deliver stimulation to the stimulation site, weighted current may be applied simultaneously or in a time-interleaved manner via the two adjacent electrodes.

Figure 11:
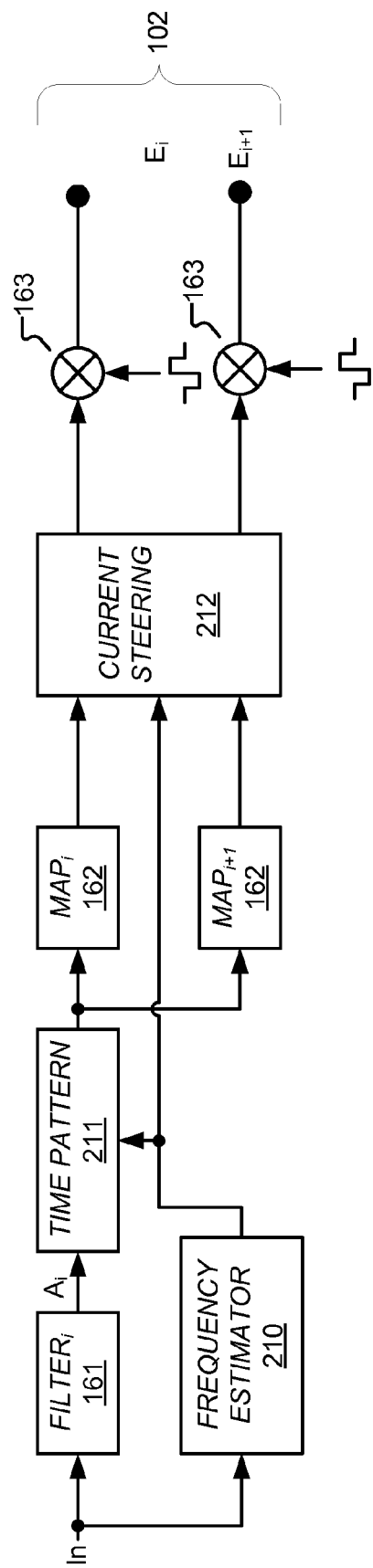
FIG. 11 is a functional block diagram of an exemplary current-steering strategy as applied via a single channel within an implantable stimulator according to principles described herein.

FIG. 11 is a functional block diagram of an exemplary current-steering strategy as applied via a single channel within an implantable stimulator. A single channel is shown within FIG. 11 for illustrative purposes only. It will be recognized that any number of channels within an implantable stimulator may be configured to apply stimulation in accordance with a current-steering strategy.

As shown in FIG. 11, an input signal is filtered by one or more filters 161 configured to divide the signal into a number of frequency channels or bands, as described in connection with FIG. 6. The input signal is also input into a frequency estimator 210 configured to estimate the peak frequency thereof. A time pattern block 211 is configured to build construct the temporal structure of a pulse train representing the signal output by the filter 161.

Mapping stages 162 are configured to map the amplitude of the signal output by the time pattern block 211 to corresponding current levels in accordance with a suitable mapping function, as described in connection with FIG. 6.

The output of each mapping stage 162 is input into a current-steering block 212. The current-steering block 212 is also configured to receive the output of the frequency estimator 210. In some examples, the current-steering block 212 is configured to determine appropriate weighting factors for current to be applied via two adjacent electrodes $E_i$ and $E_{i+1}$. This determination may be based at least in part on the peak frequency estimate and the output of each of the mapping functions 162. In this manner, stimulation current may be delivered to a stimulation site located in between electrodes $E_i$ and $E_{i+1}$.

Figure 12:
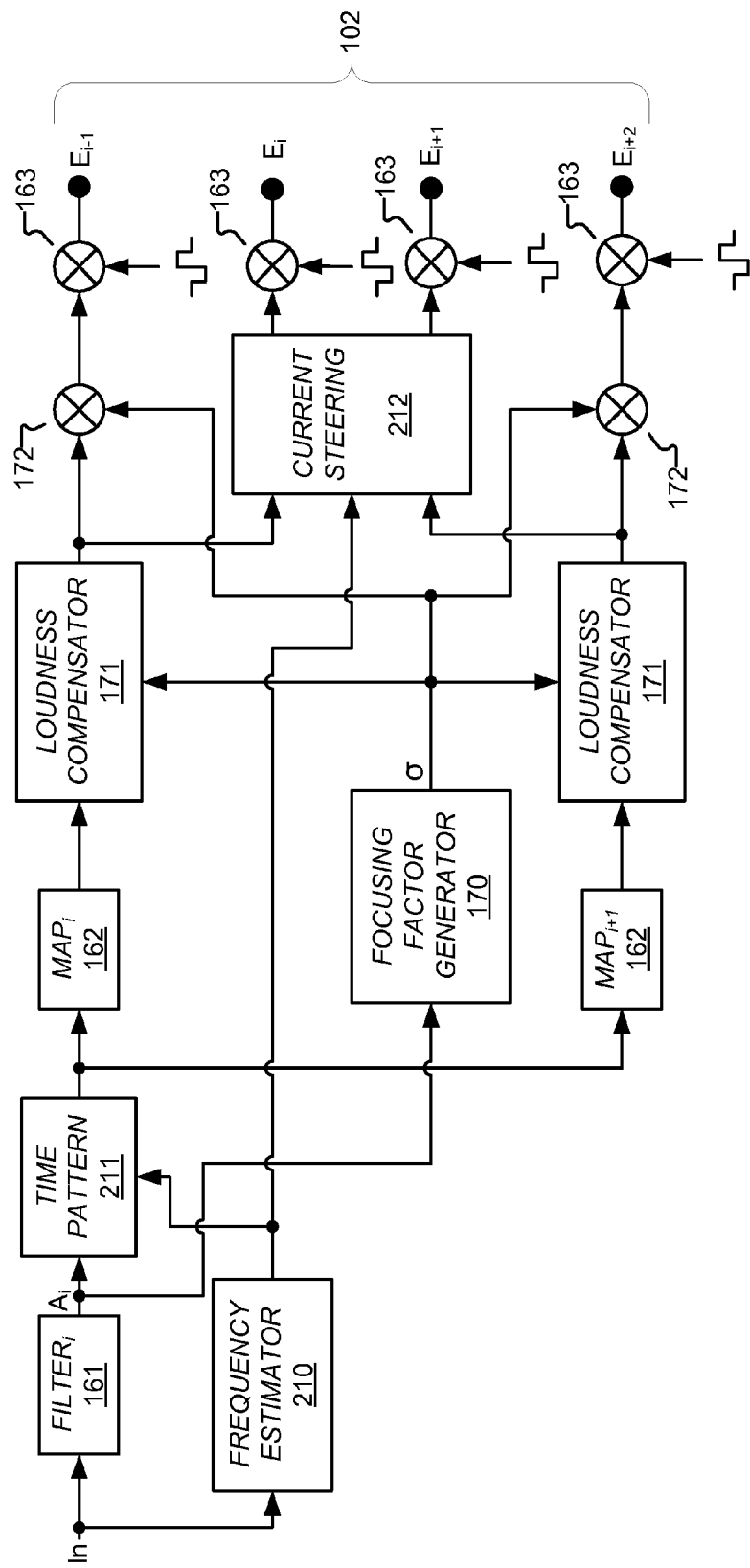
FIG. 12 illustrates an exemplary system configured to dynamically focus one or more excitation fields produced by current-steering electrodes according to principles described herein.

The excitation field produced by the current-steering electrodes $E_i$ and $E_{i+1}$ may be narrowed by applying compensating current simultaneously or in a time-interleaved manner via one or more additional electrodes 102. FIG. 12 illustrates an exemplary system configured to dynamically focus one or more excitation fields produced by current-steering electrodes. It will be recognized that the system shown in FIG. 12 is merely exemplary and that it may include additional or alternative components and/or functions.

The system of FIG. 12 includes many of the same components as the system of FIG. 11. In addition, the system of FIG. 12 includes a focusing factor generator 170 configured to generate the aforementioned focusing factor σ based on the amplitude of the signal output by the filter 161. The focusing factor σ is used to generate scaled versions of the current steering current. This scaled current is delivered via one or more additional electrodes (e.g., $E_{i-1}$ and $E_{i+2}$) to effectively narrow the excitation field produced by electrodes $E_i$ and $E_{i+1}$.

As shown in FIG. 12, loudness compensators 171 may also be included within the system of FIG. 12. The loudness compensators 171, as described in connection with FIG. 7, are configured to adjust the amplitudes of the currents applied via electrodes $E_i$ and $E_{i+1}$ to compensate for loudness changes that may be caused by current delivered via the compensating electrodes $E_{i-1}$ and $E_{i+2}$.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
   simultaneously applying, by an implantable stimulator, stimulation current to a stimulation site within a patient via at least one stimulating electrode and compensating current via one or more additional electrodes of opposite polarity as the at least one stimulating electrode, the compensating current configured to affect at least one excitation field caused by the stimulation current; and
   dynamically adjusting, by the implantable stimulator, the simultaneously applied compensating current as a function of a stimulation level of the stimulation current by increasing a stimulation level of the compensating current if the stimulation level of the stimulation current decreases and decreasing the stimulation level of the compensating current if the stimulation level of the stimulation current increases.

2. The method of claim 1, further comprising generating, by the implantable stimulator, a focusing factor as a function of the stimulation level of the stimulation current and using the focusing factor to generate the compensating current.

3. The method of claim 1, wherein the one or more additional electrodes comprise at least two electrodes of opposite polarity as the at least one stimulating electrode.

4. The method of claim 1, wherein the at least one stimulating electrode comprises at least two electrodes configured to apply the stimulation current in accordance with a current-steering strategy.

5. The method of claim 1, further comprising adjusting, by the implantable stimulator, the stimulation current and the compensating current with a loudness compensator to maintain equivalent loudness as perceived by the patient.

6. The method of claim 1, wherein the implantable stimulator comprises one of a cochlear implant system, an implantable pulse generator, a spinal cord stimulator, a deep brain stimulator, and a microstimulator.

7. The method of claim 1, wherein the stimulation level of the compensating current comprises an amplitude of the compensating current.

8. The method of claim 1, wherein the increasing of the stimulation level of the compensating current is configured to narrow the at least one excitation field caused by the stimulation current.

9. The method of claim 1, wherein the decreasing of the stimulation level of the compensating current is configured to minimize an effect of side lobes within a spatial pattern of the at least one excitation field caused by the stimulation current.

10. A method comprising:
simultaneously applying, by a cochlear implant system, stimulation current via at least two stimulating electrodes in accordance with a current-steering strategy and compensating current via one or more additional electrodes of opposite polarity as the at least two stimulating electrodes, the compensating current configured to affect at least one excitation field caused by the stimulation current; and
dynamically adjusting, by the cochlear implant system, the simultaneously applied compensating current as a function of a stimulation level of the stimulation current by increasing a stimulation level of the compensating current if the stimulation level of the stimulation current decreases and decreasing the stimulation level of the compensating current if the stimulation level of the stimulation current increases.

11. The method of claim 10, further comprising generating, by the cochlear implant system, a focusing factor as a function of the stimulation level of the stimulation current and using the focusing factor to generate the compensating current.

12. A system comprising:
an implantable stimulator;
at least one stimulating electrode electrically coupled to the implantable stimulator; and
one or more additional electrodes electrically coupled to the implantable stimulator;
wherein the implantable stimulator is configured to:
simultaneously apply stimulation current to a stimulation site within a patient via the at least one stimulating electrode and compensating current via the one or more additional electrodes of opposite polarity as the at least one stimulating electrode, the compensating current configured to affect at least one excitation field caused by the stimulation current; and
dynamically adjust the simultaneously applied compensating current as a function of a stimulation level of the stimulation current by increasing a stimulation level of the compensating current if the stimulation level of the stimulation current decreases and decreasing the stimulation level of the compensating current if the stimulation level of the stimulation current increases.

13. The system of claim 12, wherein the implantable stimulator is further configured to generate a focusing factor as a function of the stimulation level of the stimulation current and use the focusing factor to generate the compensating current.

14. The system of claim 12, wherein the one or more additional electrodes comprise at least two electrodes of opposite polarity as the at least one stimulating electrode.

15. The system of claim 12, wherein the at least one stimulating electrode comprises at least two electrodes configured to apply the stimulation current in accordance with a current-steering strategy.

16. The system of claim 12, wherein the implantable stimulator is further configured to adjust the stimulation current and the compensating current to maintain equivalent loudness as perceived by the patient.

17. The system of claim 12, wherein the implantable stimulator comprises one of a cochlear implant system, an implantable pulse generator, a spinal cord stimulator, a deep brain stimulator, and a microstimulator.

18. The system of claim 12, wherein the stimulation level of the compensating current comprises an amplitude of the compensating current.

19. The system of claim 12, wherein the increasing of the stimulation level of the compensating current is configured to narrow the at least one excitation field caused by the stimulation current.

20. The system of claim 12, wherein the decreasing of the stimulation level of the compensating current is configured to minimize an effect of side lobes within a spatial pattern of the at least one excitation field caused by the stimulation current.

* * * * *